US012733826B2

(12) United States Patent
Hong et al.

(10) Patent No.: US 12,733,826 B2
(45) Date of Patent: Sep. 15, 2026

(54) METHOD AND DEVICE FOR DETECTING HEART RATE USING PHOTOPLETHYSMOGRAPHY SIGNAL WITH REMOVED MOTION ARTIFACT

(71) Applicant: SAMSUNG LIFE PUBLIC WELFARE FOUNDATION, Seoul (KR)

(72) Inventors: Sung Jun Hong, Seoul (KR); Tae Kyung Kim, Seoul (KR); Min Hee Kang, Seoul (KR); Hyo Chang Seo, Seoul (KR); Young Min Shon, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 0 days.

(21) Appl. No.: 18/911,379

(22) Filed: Oct. 10, 2024

(65) Prior Publication Data

US 2025/0031985 A1 Jan. 30, 2025

Related U.S. Application Data

(63) Continuation of application No. PCT/KR2023/018775, filed on Nov. 21, 2023.

(30) Foreign Application Priority Data

Jul. 26, 2023 (KR) ........................ 10-2023-0097342

(51) Int. Cl.
*A61B 5/024* (2006.01)
*A61B 5/00* (2006.01)

(52) U.S. Cl.
CPC .......... *A61B 5/02416* (2013.01); *A61B 5/721* (2013.01); *A61B 5/7246* (2013.01); *A61B 5/7257* (2013.01); *A61B 5/7264* (2013.01); *A61B 5/7271* (2013.01); *A61B 2562/0219* (2013.01)

(58) Field of Classification Search
CPC ........ A61B 2562/0219; A61B 5/02416; A61B 5/0816; A61B 5/11; A61B 5/721; A61B 5/7246; A61B 5/7257; A61B 5/7264; A61B 5/7271
See application file for complete search history.

(56) References Cited

U.S. PATENT DOCUMENTS

2016/0367158 A1 12/2016 Samadani et al.

FOREIGN PATENT DOCUMENTS

| | | | |
|---|---|---|---|
| KR | 1020100062736 | A | 6/2010 |
| KR | 1020100065084 | A | 6/2010 |
| KR | 1020160114893 | A | 10/2016 |
| KR | 1020200080755 | A | 7/2020 |
| WO | 2015044010 | A1 | 4/2015 |

*Primary Examiner* — Mark D Remaly
(74) *Attorney, Agent, or Firm* — The Webb Law Firm

(57) ABSTRACT

A method of detecting a heart rate using a photoplethysmography (PPG) signal with a removed motion artifact includes receiving, by a heart rate measurement device, a PPG signal and an acceleration signal; converting, by the heart rate measurement device, the PPG signal and the acceleration signal into signals in a frequency domain; calculating, by the heart rate measurement device, a difference between the PPG signal and the acceleration signal in the frequency domain and obtaining a PPG signal with a removed motion artifact; and estimating, by the heart rate measurement device, a heart rate based on the PPG signal with the removed motion artifact.

8 Claims, 4 Drawing Sheets

10

METHOD AND DEVICE FOR DETECTING HEART RATE USING PHOTOPLETHYSMOGRAPHY SIGNAL WITH REMOVED MOTION ARTIFACT

CROSS-REFERENCE TO RELATED APPLICATIONS

This application is a Bypass Continuation Application of International Patent Application No. PCT/KR2023/018775 filed Nov. 21, 2023, and claims priority to Korean Patent Application No. 10-2023-0097342 filed Jul. 26, 2023, the disclosures of which are hereby incorporated by reference in their entireties.

BACKGROUND OF THE INVENTION

Field of the Invention

The present invention relates to a method of detecting a heart rate using photoplethysmography (PPG).

Description of Related Art

Recently, various types of wearable devices (smart watches, smart glasses, and the like) have been released. Various sensors are attached to wearable devices and may measure various biological signals.

Photoplethysmography (PPG) sensors may be attached to the wearable devices. PPG is one method of detecting a heart rate by detecting changes of a blood flow rate using light. In PPG, light (infrared or red light) passes through a finger or earlobe, and then an amount of reflected or transmitted light is measured using a light-receiving sensor. PPG is also widely used to analyze diseases such as cardiovascular disease and vascular elasticity.

RELATED ART DOCUMENT

Patent Document

Korean Patent Laid-Open Application No. 10-2010-0062736

SUMMARY OF THE INVENTION

Technical Problem

The conventional technique of estimating a heart rate using photoplethysmography (PPG) detects an R-peak of a PPG signal that changes according to systole and detects the heart rate that changes in real time. However, the PPG measured from a wearable device includes a motion artifact. The motion artifact is a noise caused by the movement or hand tremor of a wearer of the wearable device. Since a frequency band for the motion artifact overlaps a frequency band for the PPG, quality of the PPG signal is degraded, and thus accuracy of heart rate estimation is reduced.

The present invention, which will be described below, provides a method of accurately measuring a heart rate by removing a motion artifact from a PPG signal.

Technical Solution

A method of detecting a heart rate using a photoplethysmography (PPG) signal with a removed motion artifact includes receiving, by a heart rate measurement device, a PPG signal and an acceleration signal; converting, by the heart rate measurement device, the PPG signal and the acceleration signal into signals in a frequency domain; calculating, by the heart rate measurement device, a difference between the PPG signal and the acceleration signal in the frequency domain and obtaining a PPG signal with a removed motion artifact; and estimating, by the heart rate measurement device, a heart rate based on the PPG signal with the removed motion artifact.

Advantageous Effects

According to the present invention which will be described below, a heart rate can be measured using a heart rate measurement device. The heart rate measurement device can be a wearable device. Therefore, the heart rate can be measured based on values measured by a photoplethysmography (PPG) sensor and an acceleration sensor, which are attached to the wearable device.

According to the present invention which will be described below, a heart rate can be measured using a PPG signal with a removed motion artifact In this way, a user can measure a heart rate more accurately.

DESCRIPTION OF THE INVENTION

Figure 1:
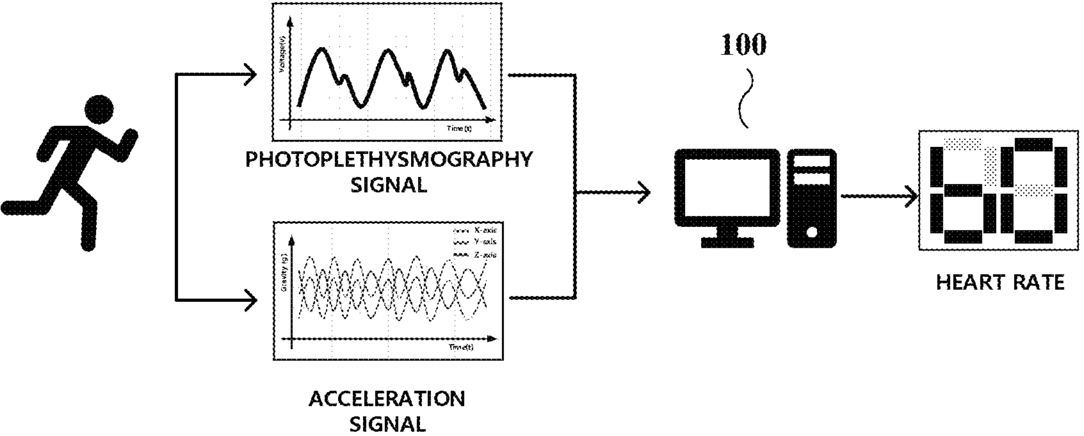
FIG. 1 is a diagram illustrating an overall process (10) in which a heart rate measurement device (100) detects a heart rate using a photoplethysmography (PPG) signal with a removed motion artifact.

The present invention, which will be described below, may be variously modified and may have various embodiments. Specific embodiments of the present invention, which will be described below, may be set forth in the drawings of the present specification. However, this is for the purpose of describing the present invention, which will be described below, and is not intended to limit the present invention to a specific embodiment. Therefore, it should be construed that all modifications, equivalents or substitutes included in the spirit and scope of the present invention, which will be described below, are included in the present invention.

Hereinafter, the singular form should be understood to include the plural form unless the context clearly dictates otherwise, and the terms "comprising," "having," and the like are used to specify the presence of features, numbers, steps, operations, components, elements, or combinations thereof described herein, but do not preclude the presence or addition of one or more other features, numbers, steps, operations, components, elements, or combinations thereof.

Before describing the drawings in detail, it should be noted that the classification of constituent parts in the present specification is merely classification for a main function of each of the constituent parts. That is, two or more constituent parts described below may be combined into a single constituent part, or a single constituent part may be divided into two or more constituent parts according to a more subdivided function. Further, each of the constituent parts described below may additionally perform some or all functions of other constituent parts in addition to its main function, and some of the main function of each of the constituent parts may also be exclusively carried out by other constituent parts.

In addition, in performing a method or an operating method, processes constituting the method may be performed in a different order from the specified order unless a specific order is clearly described in context. That is, the processes may be performed in the same order as specified, may be performed substantially simultaneously, or may be performed in reverse order.

Hereinafter, the overall process by which a heart rate measurement device performs a heart rate detection method using a photoplethysmography (PPG) signal with a removed motion artifact will be described.

FIG. 1 is a diagram illustrating an overall process 10 in which a heart rate measurement device 100 detects a heart rate using a PPG signal with a removed motion artifact.

The heart rate measurement device 100 may receive a PPG signal and an acceleration signal. The heart rate measurement device 100 may convert the PPG signal and the acceleration signal into signals in a frequency domain. The heart rate measurement device 100 may obtain a PPG signal with a removed motion artifact by calculating a difference between the PPG signal and the acceleration signal in a frequency domain. The heart rate measurement device 100 may estimate a heart rate based on the PPG signal with the removed motion artifact.

Hereinafter, a method of detecting a heart rate using a PPG signal with a removed motion artifact will be described in detail.

Figure 2:
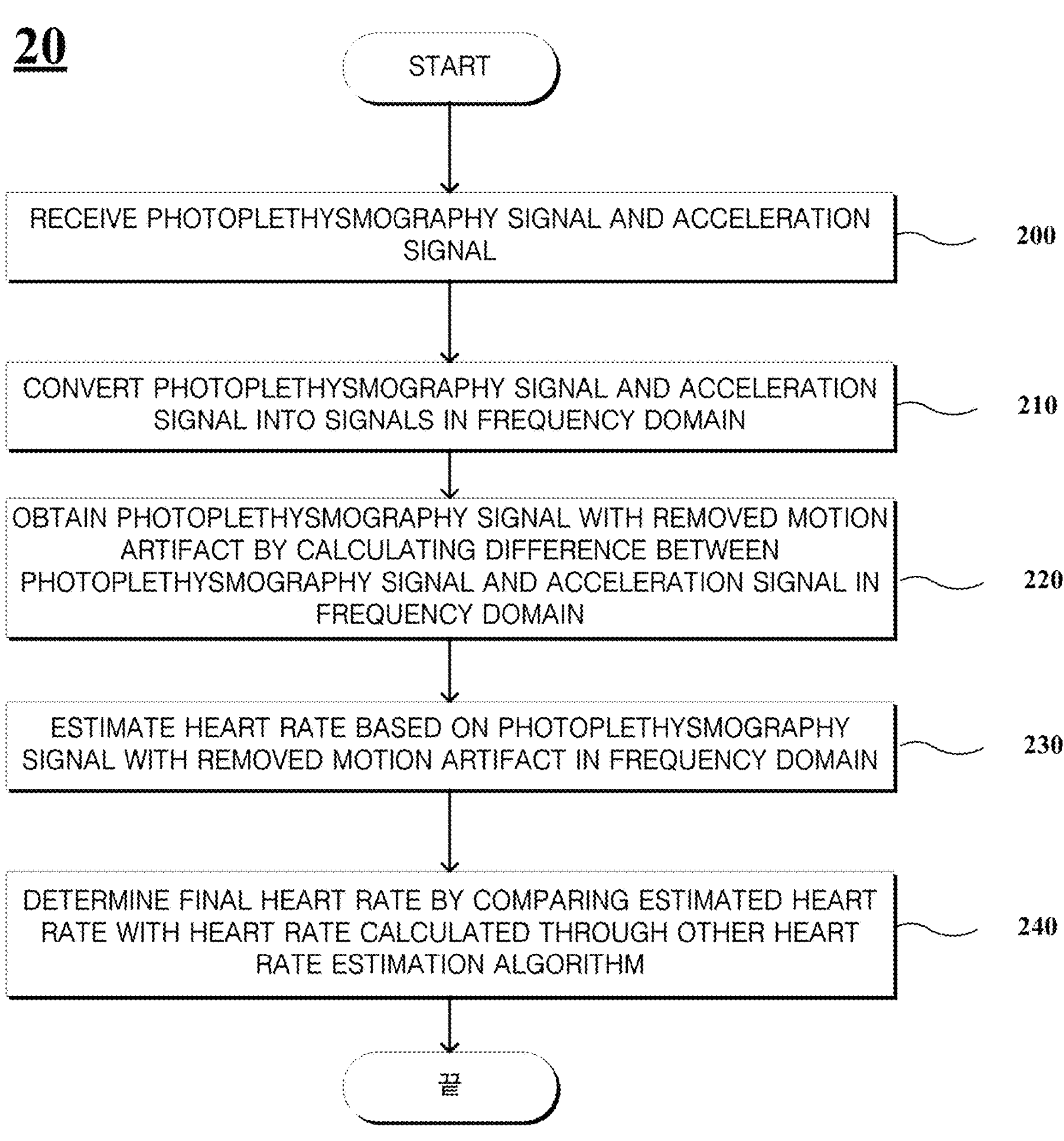
FIG. 2 is a diagram illustrating an example of a process (20) of detecting a heart rate using the PPG signal with a removed motion artifact.

FIG. 2 is a diagram illustrating an example of a process 20 of detecting a heart rate using the PPG signal with a removed motion artifact.

The heart rate measurement device may receive the PPG signal and the acceleration signal (200).

The PPG signal may be a biological signal obtained by measuring light reflected or transmitted from skin tissue after the light is emitted to subcutaneous tissue. The PPG signal may be used to determine a state of cardiac activity by measuring an amount of blood flowing through the blood vessels.

A motion artifact may be included in the PPG signal. The motion artifact may be a noise due to movement generated by hand tremors when the PPG signal is measured. When the motion artifact occurs, a change may occur in the PPG signal. The motion artifact may occur due to a change in acceleration. Information on the motion artifact may be obtained through an acceleration signal.

The acceleration signal may be information obtained by measuring movement of a user. The acceleration signal may be used to determine a degree of inclination of the user and a degree of exercise of the user. The acceleration signal may be acceleration signals on three axes (X-axis, Y-axis, and Z-axis).

The PPG and acceleration signals may be signals measured by sensors attached to a wearable device of a target user. As an example, the PPG and acceleration signals may be signals measured by sensors attached to a smart watch worn by the target user.

The heart rate measurement device may detrend oscillations of signals that are included in the received PPG signal and change due to breathing and the heart.

The heart rate measurement device may calculate a root mean square (RMS) of three-axis acceleration signal components to calculate a quantitative magnitude of the movement included in the received acceleration signal.

The heart rate measurement device may synchronize the received PPG signal and the received acceleration signal. This may be because the PPG signal and the acceleration signal are simultaneously measured signals, and thus the number of samples may be the same for comparison.

The heart rate measurement device may convert the PPG signal and the acceleration signal into signals in a frequency domain (210).

The heart rate measurement device may use a Fourier transform for conversion into a signal in a frequency domain. In this way, the heart rate measurement device may calculate a periodogram of the PPG signal and the acceleration signal to calculate a frequency magnitude of each signal component.

The heart rate measurement device may normalize the PPG signal and the acceleration signal. In this way, the heart rate measurement device unifies units of the PPG signal and the acceleration signal. For example, since a unit of the PPG signal (mV) is different from a unit of the acceleration signal ($m/s^2$), it may be difficult to compare the two signals. To this end, the two signals may be normalized.

The heart rate measurement device may assign different weight values to the PPG signal and the acceleration signal depending on a degree of movement of the user. As an example, the heart rate measurement device may assign a weight value to an acceleration signal in a frequency domain depending on a speed of the user. In this way, loss of components of the PPG signal may be minimized during signal restoration.

Equation 1 is used to normalize the acceleration signal and then assign a weight value depending on the speed of the user.

$$f'_{acc} = W_{acc} \times \left( \frac{f_{acc} - f_{pgg}^{min}}{f_{ppg}^{max} - f_{ppg}^{min}} \right) \quad \text{[Equation 1]}$$

In Equation 1, $f'_{acc}$ may be an acceleration signal in the frequency domain where the normalization process and the weight value assignment process are performed. In Equation 1, $W_{acc}$ may be a weight value assigned to the acceleration signal. In Equation 1, $f_{acc}$ may be an acceleration signal in the frequency domain. In Equation 1, $f^{min}_{acc}$ may be a minimum frequency of the PPG signal in the frequency domain. In Equation 1, $f^{max}_{pgg}$ may be a maximum frequency of the PPG signal in the frequency domain.

The heart rate measurement device may obtain a PPG signal with a removed motion artifact by calculating a difference between the PPG signal and the acceleration signal in the frequency domain (220).

As an example, the heart rate measurement device may calculate a difference between the two signals by subtracting the acceleration signal from the PPG signal in the frequency domain. In this way, a PPG signal with the removed motion artifact may be obtained by removing the acceleration signal included in the PPG signal.

Equation 2 is an example of a difference equation used when calculating the difference between the two signals.

$$f'_{ppg} = f_{ppg} - f'_{acc} \quad \text{[Equation 2]}$$

In Equation 2, $f'_{ppg}$ may be a PPG signal with a removed motion artifact in the frequency domain. In Equation 2, $f_{ppg}$ may be a PPG signal in the frequency domain. In Equation 2, $f'_{acc}$ is the acceleration signal in the frequency domain. Specifically, $f'_{acc}$ may be the acceleration signal in the frequency domain where the normalization process and the weight value assignment process of Equation 1 are performed.

The heart rate measurement device may estimate a heart rate based on the PPG signal with the removed motion artifact in the frequency domain (230).

As an example, the heart rate measurement device may estimate a heart rate by selecting a frequency of a signal with a strongest magnitude among PPG signals from which acceleration signals are removed in the frequency domain and then multiplying the corresponding frequency by a preset value. For example, when a frequency of a signal with a strongest magnitude in the periodogram of the PPG signal from which the acceleration signal is removed is 1 Hz, a current heart rate may be estimated as 60 by multiplying 1 Hz by a preset value of 60 (BPM).

The heart rate measurement device may determine a final heart rate by comparing the estimated heart rate with a heart rate calculated through the other heart rate estimation algorithm (240).

As an example, the heart rate measurement device may use an R-peak-based heart rate estimation algorithm as the other algorithm. Specifically, the heart rate measurement device may calculate the heart rate from the received PPG signal on the basis of the R-peak-based heart rate estimation algorithm. The R-peak-based heart rate estimation algorithm is one method of detecting a heart rate based on an R-peak of the PPG signal that changes due to systole.

As an example, the heart rate measurement device may calculate the difference between the estimated heart rate and the heart rate calculated through the other heart rate estimation algorithm and then determine the final heart rate based on whether a corresponding difference value is less than or equal to a threshold value. For example, when the difference between the estimated heart rate and the heart rate calculated through the other heart rate estimation algorithm is less than or equal to a threshold value, the estimated heart rate may be determined as a final heart rate. Alternatively, when the difference between the estimated heart rate and the heart rate calculated through the other heart rate estimation algorithm is greater than or equal to the threshold value, the heart rate calculated through the other heart rate estimation algorithm may be determined as the final heart rate.

Figure 3:
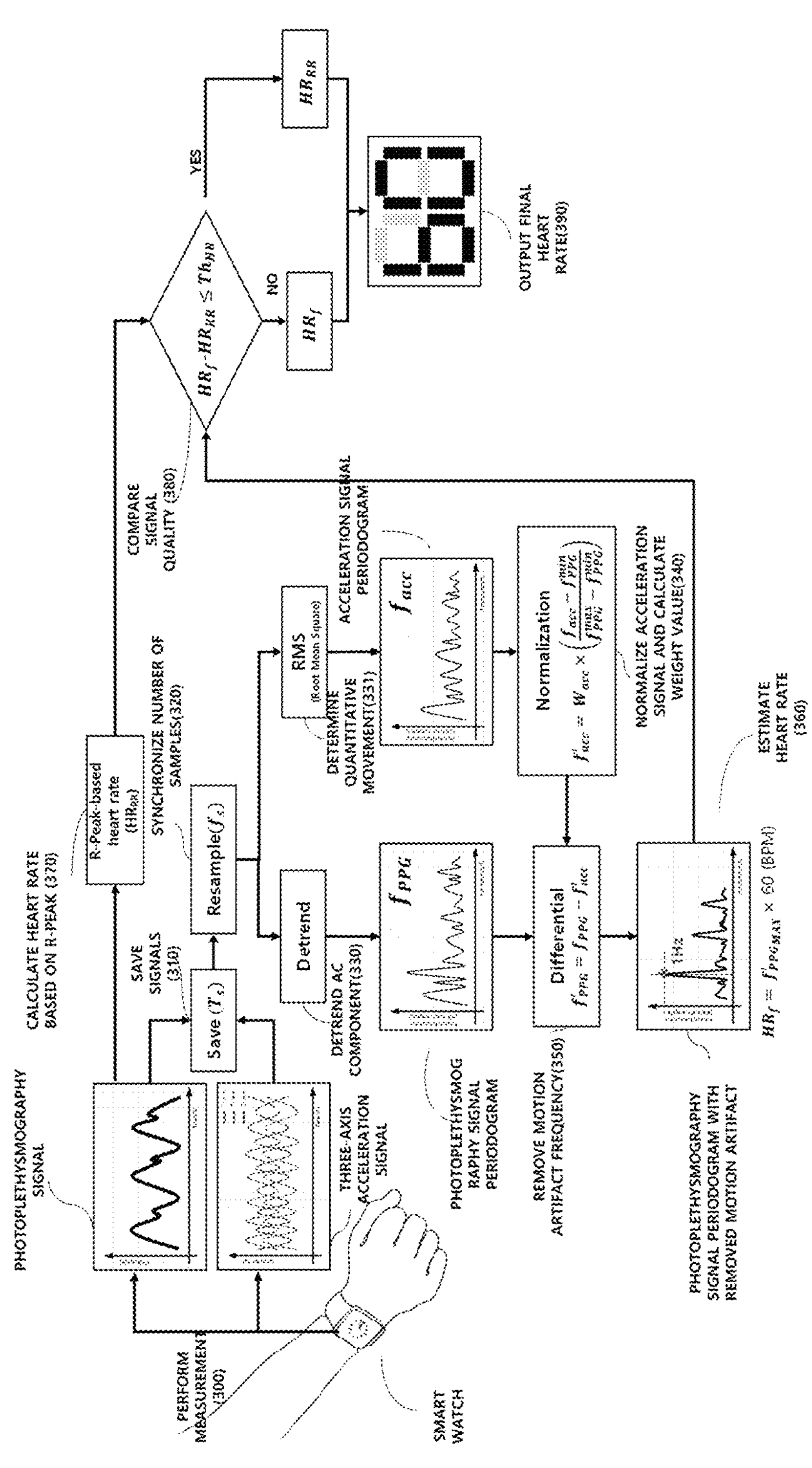
FIG. 3 is a diagram illustrating one embodiment (30) of detecting a heart rate using the PPG signal with a removed motion artifact.

FIG. 3 is a diagram illustrating one 30 embodiment of detecting a heart rate using the PPG signal with a removed motion artifact. FIG. 3 is one example using a smart watch as the heart rate measurement device.

The smart watch may receive a PPG signal and a three-axis acceleration signal, which are measured by a sensor (300). The three-axis acceleration signal may include acceleration signals on an x-axis, a y-axis, and a z-axis.

The smart watch may save the received PPG signal and the received three-axis acceleration signal (310).

The smart watch may synchronize (resample) the PPG signal and the three-axis acceleration signal (320). That is, the PPG signal and the three-axis acceleration signal are signals measured simultaneously by a wearable device, and in order to equalize a size of the frequency domain, synchronization (320) may be performed so that the number of samples is the same.

The smart watch may detrend an AC component from the PPG signal (330). The smart watch may determine quantitative movement by calculating an RMS of the three-axis acceleration signal (331).

The smart watch may detect a PPG signal in the frequency domain and determine a periodogram of the PPG signal. The smart watch may detect an acceleration signal in the frequency domain and determine a periodogram of the acceleration signal.

The smart watch may normalize the acceleration signal in the frequency domain and then calculate and assign a weight value (340). That is, the smart watch may normalize the acceleration signal in the frequency domain using Equation 1 and then assign the weight value.

The smart watch may obtain a PPG signal with a removed motion artifact frequency by subtracting the acceleration signal from the PPG signal (350). To this end, the smart watch may use the differential equation of Equation 2.

The smart watch may estimate a heart rate by selecting a frequency with the strongest signal of the PPG signals with removed motion artifact frequencies in the frequency domain and then multiplying the frequency by a preset value (360). That is, the smart watch may select a frequency of 1 Hz with the strongest signal and then multiply the selected frequency by a preset value of 60 (BPM) to estimate that a current heart rate is 60.

The smart watch may calculate a heart rate $HR_{RR}$ using the received PPG signal (310) through the R-peak-based heart rate algorithm which is the other heart rate estimation algorithm (370).

The smart watch may compare the estimated heart rate with the heart rate calculated through the above-described R-peak-based heart rate algorithm (380). That is, the smart watch may calculate whether a difference value between an estimated heart rate $HR_f$ and a heart rate $HR_{RR}$ calculated through the R-peak-based heart rate algorithm is greater/less than or equal to a threshold value $Th_{HR}$.

When the difference value is less than or equal to the threshold value, the smart watch may output the estimated heart rate $HR_f$ as a final heart rate. On the other hand, when the difference value is greater than or equal to the threshold value, the smart watch may output the heart rate $HR_{RR}$ calculated through the R-peak-based algorithm as the final heart rate (390).

Hereinafter, the heart rate measurement device will be described.

Figure 4:
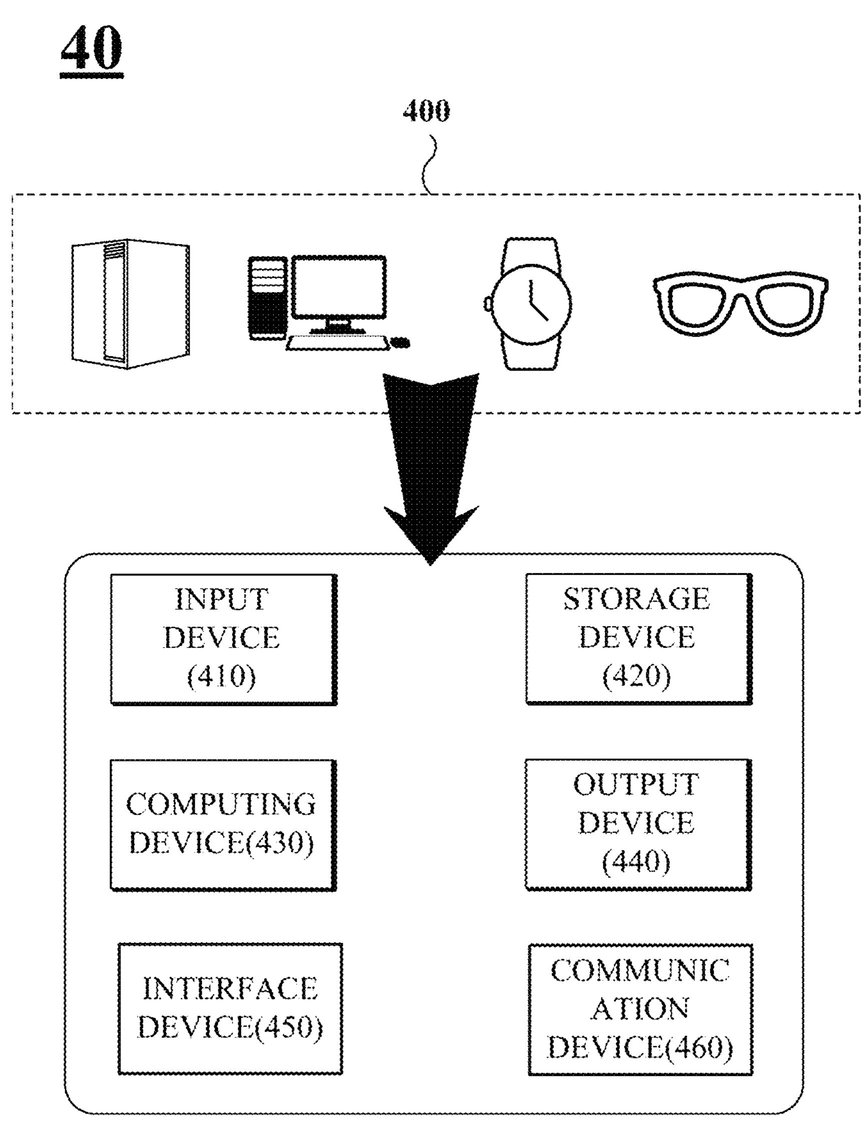
FIG. 4 is a diagram illustrating a configuration (40) of one embodiment of a heart rate measurement device (400).

FIG. 4 is a diagram illustrating a configuration 40 of one embodiment of a heart rate measurement device 400.

The heart rate measurement device 400 may correspond to the heart rate measurement device 100 described in FIG. 1. The heart rate measurement device 400 may be a device for performing the above-described method of detecting a heart rate using a PPG signal with a removed motion artifact.

The heart rate measurement device 400 may be physically implemented in various forms. For example, the heart rate measurement device 400 may be implemented in the form of a personal computer (PC), a laptop, a server, or a dedicated data processing chipset. Alternatively, the heart rate measurement device 400 may be implemented in the form of wearable devices (a smart watch, smart glasses, a smart ring, and the like).

The heart rate measurement device 400 may include an input device 410, a storage device 420, a computing device 430, an output device 440, an interface device 450, and a communication device 460.

The input device 410 may include interface devices (a keyboard, a mouse, and a touch screen) for receiving predetermined commands or data. The input device 410 may also include a configuration for receiving information through separate storage devices (a universal serial bus (USB), a compact disc (CD), a hard disk, and the like). The input device 410 may receive input data through a separate measuring device or a separate database (DB). The input device 410 may receive data through wired or wireless communication. The input device 410 may be connected to a sensor and may receive data measured by the sensor.

The input device 410 may receive biological signals, information, and models, which are required for performing a method of detecting a heart rate using a PPG signal with a removed motion artifact. The input device 410 may receive a PPG signal. The input device 410 may receive an acceleration signal.

The storage device 420 may store information received through the input device 410. The storage device 420 may store information generated during a computational process of the computing device 430. That is, the storage device 420 may include a memory. The storage device 420 may store a result calculated by the computing device 430.

The storage device 420 may store biological signals, information, and models, which are required for performing a method of detecting a heart rate using the above-described PPG signal with the removed motion artifact. The storage device 420 may store a PPG signal. The storage device 420 may store an acceleration signal.

The computing device 430 may be a device such as a processor, an application processor (AP), or a chip embedded with a program, which processes data and performs predetermined arithmetic operations. The computing device 430 may generate a control signal for controlling the heart rate measurement device.

The computing device 430 may perform an arithmetic operation required for performing the method of detecting a heart rate using a PPG signal with a removed motion artifact.

The computing device 430 may convert the PPG signal and the acceleration signal into signals in a frequency domain. The computing device 430 may obtain a PPG signal with a removed motion artifact by calculating a difference between the PPG signal and the acceleration signal in the frequency domain. The computing device 430 may estimate a heart rate based on the PPG signal with the removed motion artifact.

The output device 440 may be a device which outputs predetermined information. The output device 440 may also output interfaces required for data processing, input data, analysis results, and the like. The output device 440 may be physically implemented in various forms, such as a display, a device for outputting a document, and the like.

The output device 440 may output the heart rate estimated by the computing device 430. For example, the output device 440 may be a display of a smart watch and may output the heart rate estimated by the computing device 430 to the display.

The interface device 450 may be a device which receives predetermined commands and data from an external device. The interface device 450 may receive information required for performing the method of detecting a heart rate using a PPG signal with a removed motion artifact from a physically connected input device or an external storage device. The interface device 450 may receive the control signal for controlling the heart rate measurement device 400. The interface device 450 may output a result analyzed by the heart rate measurement device 400.

The communication device 460 may be a component which receives and transmits predetermined information through a wired or wireless network. The communication device 460 may receive the control signal required for controlling the heart rate measurement device 400. The communication device 460 may transmit the result analyzed by the heart rate measurement device 400.

The above-described method of detecting a heart rate using a PPG signal with a removed motion artifact may be implemented as a program (or application) including an executable algorithm that can be run on a computer.

The program may be stored and provided in a transitory or non-transitory computer readable medium.

The non-transitory computer readable medium may be a medium which stores data semi-permanently and is readable by a device instead of a medium which stores data for a short period of time, such as a register, a cache, or a memory. Specifically, various applications or programs described above may be stored and provided in non-transitory readable media such as compact discs (CDs), digital versatile discs (DVDs), hard disks, blu-ray discs, universal serial buses (USBs), memory cards, read-only memories (ROMs), programmable ROMs (PROMs), erasable PROMs (EPROMs), electrically EPROMs (EEPROMs), and flash memories.

The transitory readable media include various random access memories (RAMs) such as static RAMs (SRAMs), dynamic RAMs (DRAMs), synchronous DRAMs (SDRAMs), double data rate SDRAMs (DDR SDRAMs), enhanced SDRAMs (ESDRAMs), synclink DRAMs (SL-DRAMs), and direct rambus RAMs (DRRAMs).

The present embodiments and the accompanying drawings of the present specification clearly show only some of the technical ideas included in the present invention, and it should be apparent that all modified examples and specific embodiments, which can be easily inferred by those skilled in the art within the scope of the technical idea included in the present specification and the accompanying drawings of the present invention, are included in the scope of the present invention.

The invention claimed is:

1. A device for detecting a heart rate using a photoplethysmography (PPG) signal with a removed motion artifact, the device comprising:

an input device which receives a PPG signal and an acceleration signal;

a computing device configured to convert the PPG signal and the acceleration signal into signals in a frequency domain, calculate a difference between the PPG signal and the acceleration signal in the frequency domain to obtain a PPG signal with a removed motion artifact, and estimate a heart rate based on the PPG signal with the removed motion artifact; and a storage device configured to store the PPG signal and the acceleration signal, wherein the computing device assigns a weight value to the acceleration signal converted into the signal in the frequency domain depending on a speed of the user.

2. The device of claim 1, wherein the acceleration signal includes an acceleration signal in each of X-axis, Y-axis, and Z-axis directions.

3. The device of claim 1, wherein the computing device detrends oscillations of signals that are included in the received PPG signal and change due to breathing and the heart.

4. The device of claim 1, wherein the computing device normalizes the acceleration signal converted into the signal in the frequency domain and unifies a unit with a unit of the PPG signal in the frequency domain.

5. The device of claim 1, wherein the computing device estimates the heart rate by selecting a frequency of a signal with a strongest magnitude among PPG signals from which acceleration signals are removed in the frequency domain and then multiplying the selected frequency by a preset value.

6. The device of claim 1, wherein the computing device determines a final heart rate by comparing the estimated heart rate with a heart rate calculated through the other heart rate estimation algorithm.

7. The device of claim 6, wherein the other heart rate estimation algorithm includes an algorithm of estimating a heart rate based on an R-peak of the PPG signal that changes due to systole.

8. The device of claim 6, wherein the computing device determines the final heart rate by calculating a difference value between the estimated heart rate and the heart rate calculated through the other heart rate estimation algorithm, determining the estimated heart rate as the final heart rate when the calculated difference value is less than or equal to a preset threshold value, and determining the heart rate calculated through the other heart rate estimation algorithm as the final heart rate when the calculated difference value is greater than or equal to the preset threshold value.

* * * * *